United States Patent
Caruba et al.

(10) Patent No.: US 8,378,306 B2
(45) Date of Patent: Feb. 19, 2013

(54) DUAL AMPLIFIER FOR MR-PET HYBRID IMAGING SYSTEM

(75) Inventors: James Frank Caruba, Bartlett, IL (US); Roger E. Arseneau, Buffalo Grove, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 13/186,950

(22) Filed: Jul. 20, 2011

(65) Prior Publication Data

US 2012/0018643 A1 Jan. 26, 2012

Related U.S. Application Data

(60) Provisional application No. 61/366,272, filed on Jul. 21, 2010, provisional application No. 61/366,267, filed on Jul. 21, 2010.

(51) Int. Cl.
*G01T 1/10* (2006.01)
(52) U.S. Cl. ........................................ 250/362
(58) Field of Classification Search ................ 250/362, 250/363.01–363.1; 600/509
See application file for complete search history.

(56) References Cited

U.S. PATENT DOCUMENTS

| | | | |
|---|---|---|---|
| 5,672,877 A | 9/1997 | Liebig et al. | |
| 2005/0113667 A1 | 5/2005 | Schlyer et al. | |
| 2005/0277826 A1* | 12/2005 | Dunseath, Jr. | 600/410 |
| 2007/0130554 A1 | 6/2007 | Caruba | |
| 2008/0204028 A1* | 8/2008 | DeVries et al. | 324/322 |
| 2010/0076300 A1 | 3/2010 | Arseneau et al. | |

OTHER PUBLICATIONS

Raylman et al., "Initial tests of a prototype MRI-compatiable PET imager," 2006, Nuclear Instruments and Methods in Physics Research A, vol. 569, pp. 306-309.*
Huh et al., "Development of filtering methods for PET signals contaminated by RF pulses for combined PET-MRI," 2009, IEEE Nuclear Science Symposium Conference Record, vol. M13-258, pp. 3812-3815.*
Herzog et al., "The current state, challenges and perspectives of MR-PET," 2010, NeuroImage, vol. 49, pp. 2072-2082.*
Laudon et al., "Minimizing interference from Magnetic Resonance Imagers during Electrocardiography," 1998, IEEE Transactions on Biomedical Engineering, vol. 45, No. 2, pp. 160-164.*

* cited by examiner

*Primary Examiner* — Kiho Kim
(74) *Attorney, Agent, or Firm* — Peter Kendall

(57) ABSTRACT

PET signals are amplified in a hybrid PET/MR system. An amplifier structure is provided for operation in the magnetic field of the MR magnets. By filtering to remove signals at the MR frequency (e.g., about 123 MHz) as part of the amplification circuit, the amplification circuit may be positioned within the RF cabin, within the magnetic field, and even within a same housing as the MR magnets. MR interference may be reduced by staged amplification. The filtering may be bi-directional, such as using parallel and series traps. Digitization of the PET signals may be provided within the magnetic field with no or little interference with MR operation.

20 Claims, 2 Drawing Sheets

DUAL AMPLIFIER FOR MR-PET HYBRID IMAGING SYSTEM

CROSS-REFERENCES TO RELATED APPLICATIONS

This application claims the benefit of U.S. provisional applications entitled "Power Distribution for Hybrid Imaging," filed Jul. 21, 2010, and assigned Ser. No. 61/366,267, and entitled "Board-Level Partitioning for Hybrid Imaging," filed Jul. 21, 2010, and assigned Ser. No. 61/366,272, the entire disclosures of which are hereby incorporated by reference.

BACKGROUND

The present embodiments relate to amplification of positron emission tomography (PET) signals.

PET may be combined with another imaging modality in a hybrid system. Such multimodality imaging systems may have diagnostic and business value. Both PET/computed tomography (CT) and single photon emission computed tomography (SPECT)/CT multimodality imaging systems allow scans to be performed back-to-back or in a same coordinate system and similar timing. The axial fields of view of the individual modalities are as close together as possible in order to minimize the impact of patient motion and increase correlation of the respective data sets.

Another hybrid example is a brain scan PET system integrated with a magnetic resonance (MR) system. In order for the MR and PET fields of view to overlap, the PET detectors are placed within the MR field of view, as an insert in front of the body coil. The MR body coil is used to excite the hydrogen molecules of the patient by delivering an RF burst. The MR switches into a receive mode, after delivery of the RF burst, and detects RF signals emitted from the patient. The signal-to-noise ratio of the MR received signal is critical to MR image quality. The signal-to-noise ratio is important enough that the MR is typically enclosed in an RF cabin that suppresses RF signals by 100 dB, for both external signals getting into the RF cabin and internal signals getting out of the RF cabin.

Electromagnetic Interference (EMI) and electromagnetic compatibility (EMC) between the MR and PET subsystems is one of the dominant technical challenges facing MR/PET. MR is extremely sensitive to any RF emissions from the PET subsystem, near the hydrogen spin frequency (e.g., roughly 123 MHz+/−500 KHz for a 3 Tesla system). Likewise, the PET front end is extremely vulnerable to the RF emissions from the MR. Coincidence windows of 4-6 nS are typical of non time-of-flight PET scanners, which require that the PET signal chain be stable to 100 pS. For the brain scan PET/MR system, the detector signals are routed out of the RF cabin to avoid EMI and EMC with the MR system. Outside the cabin, the signals are amplified and then passed through an elliptical filter. However, the number and size of cables grows in proportion to the number of PET block detectors.

BRIEF SUMMARY

By way of introduction, the preferred embodiments described below include methods, systems, and circuits for amplifying PET signals in a hybrid PET/MR system. An amplifier structure is provided for operation in the magnetic field of the MR magnets. By filtering to remove signals at the MR frequency (e.g., about 123 MHz) as part of the amplification circuit, the amplification circuit may be positioned within the RF cabin, within the magnetic field, and even adjacent to the housing of the MR magnet. The filtering may be bi-directional, such as using parallel and series traps. Passive high-order filtering may be provided prior to amplification and provide attenuation at the MR frequency. Digitization of the PET signals may be provided within the magnetic field.

In a first aspect, a circuit is provided for amplification in a hybrid magnetic resonance (MR) and positron emission tomography (PET) system. A first differential amplifier is for amplifying an analog signal from a photon detector. First and second filters connect with differential inputs of the first differential amplifier, respectively. The first and second filters are configured to reduce signals at a MR frequency. A second differential amplifier is driven by outputs of the first differential amplifier. Third and fourth filters connect to the outputs of the first differential amplifier and inputs of the second differential amplifier, respectively. The third and fourth filters are configured to reduce the signals at the MR frequency. A fifth filter connects between the inputs of the second differential amplifier. The fifth filter is configured to reduce the signals at the MR frequency.

In a second aspect, a hybrid magnetic resonance (MR) and positron emission tomography (PET) system is provided. A MR magnet generates a magnetic field. PET detectors are within the magnetic field. A differential amplifier circuit connects with the PET detectors and is positioned within the magnetic field. An analog-to-digital converter connects with the second amplifier and is positioned within the magnetic field.

In a third aspect, a method is provided for amplifying positron emission tomography (PET) signals in a hybrid magnetic resonance (MR) and PET system. The PET signals are bi-directionally attenuated at a MR frequency. The PET signals are amplified in at least two stages in an analog domain. The bi-directionally attenuation is performed, at least in part, between the two stages. The PET signals are converted to digital.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A hybrid PET/MR system is provided for whole body or other imaging. PET and MR image data may be acquired simultaneously with overlapping volumetric fields of view. Signals from the PET detectors, such as avalanche photo diodes, are directly digitized. Analog position and energy signals are filtered, amplified, and digitized inside the RF cabin, but may be digitized outside the RF cabin. Achieving high levels of attenuation, along the PET signal chain, in both directions is important to MR and PET image quality.

A dual balanced differential amplifier PET front end topology is provided in one embodiment. Parallel and series filter networks are integrated in the PET front end topology. The PET front end topology may provide high bi-directional attenuation at the MR frequency while minimizing the impact to PET signal slew rate and group delay. The dual balanced differential amplifiers process the detector cassette analog position and energy signals and interface the signals to the data acquisition unit (DAU) digital domain analog-to-digital converters.

Input common mode and differential mode RF noise produced by the MR may be rejected in the PET front end topology. PET position and energy signals from the avalanche photo diode block detectors are passed and band-limited. DAU digital signal processing noise is isolated and contained, limiting the noise exiting the DAU backwards through the PET analog signal chain. EMI and/or EMC interference between the MR imaging system and PET imaging system is limited, thereby maximizing the signal-to-noise ratio of each respective modality and allowing the simultaneous imaging of PET and MR.

Figure 1:
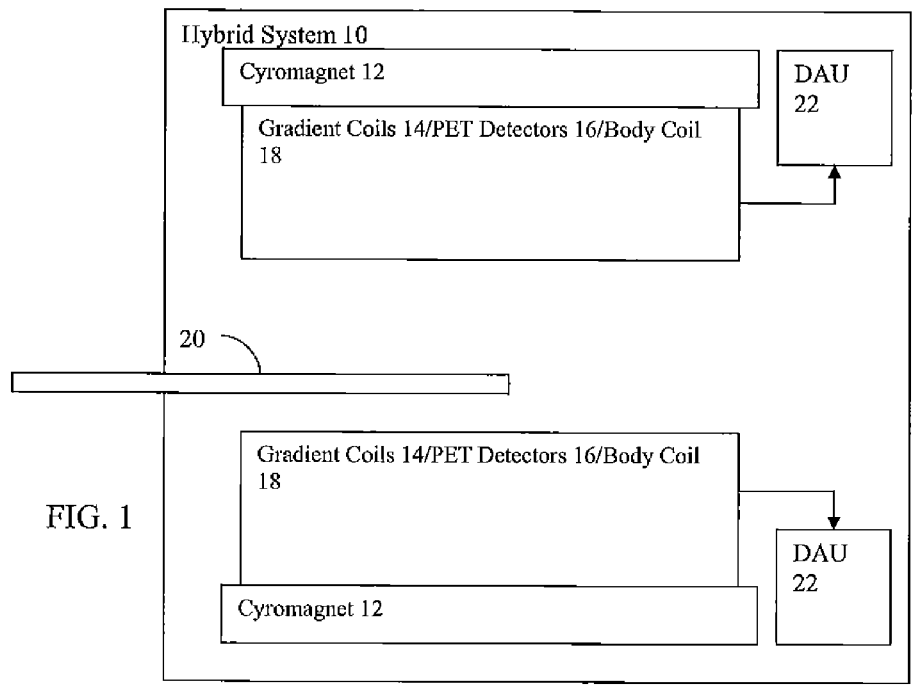
FIG. 1 is a block diagram of one embodiment of a hybrid PET/MR system.

FIG. 1 shows a hybrid magnetic resonance (MR) and positron emission tomography (PET) system 10. The hybrid PET/MR system 10 shown includes PET and MR portions. Only parts of the PET portion and parts of the MR portion are shown. Additional, different, or fewer components may be provided.

The PET and MR portions shown are integrated into one device or within a common housing. The parts of the hybrid system 10 shown in FIG. 1 are in a single freestanding unit. In other embodiments, the components of the hybrid PET/MR system 10 shown in FIG. 1 are in separate housings or separate freestanding units. For example, the DAU 22 or parts of the DAU 22 are positioned in a separate housing within the radio frequency cabin of the MR system but separate from the MR components, such as on a filter plate for routing communications and power through the RF cabin.

The PET portion is shown as the PET detectors 16 and the data acquisition unit (DAU) 22. Additional, different, or fewer components may be provided. Other parts of the PET portion may include power supplies, communications systems, image processing systems, tomography generation systems, and user interface systems. Any now known or later developed PET imaging system may be used with the modifications discussed herein. The location of the different components of the PET portion is within or outside the RF cabin, such as the image processing, tomography, power generation, and user interface components being outside the RF cabin. Power cables and fiber optic cables for communications connect the DAU 22 with the components outside the RF cabin through a filter plate.

The MR portion is shown as the cyromagnet 12, gradient coils 14, body coil 18, and patient bed 20. Additional, different, or fewer components may be provided. Other parts of the MR portion are provided within a same housing, within a same room (e.g., within the radio frequency cabin), or within a same facility. The other parts of the MR portion may include local coils, cooling systems, pulse generation systems, image processing systems, and user interface systems. Any now known or later developed MR imaging system may be used with the modifications discussed herein. The location of the different components of the MR portion is within or outside the RF cabin, such as the image processing, tomography, power generation, and user interface components being outside the RF cabin. Power cables, cooling lines, and communication cables connect the pulse generation, magnet control, and detection systems within the RF cabin with the components outside the RF cabin through a filter plate.

The cyromagnet 12, gradient coils 14, and body coil 18 are in the RF cabin, such as a room isolated by a Faraday cage. The MR portion is configured to have a tubular or laterally open examination subject bore enclosing a field of view. The patient bed 20 (e.g., a patient gurney or table) supports an examination subject such as, for example, a patient with a local coil arrangement. The patient bed 20 may be moved into the examination subject bore in order to generate images of the patient. In one embodiment, a local coil arrangement for acquiring images of a local region (e.g., the head) may be placed on or adjacent to the patient. Received signals may be transmitted by the local coil arrangement via, for example, coaxial cable or radio link (e.g., via antennas) for image generation.

In order to examine the patient using the MR portion, different magnetic fields are temporally and spatially coordinated with one another for application to the patient. The cyromagnet 12 generates a strong static main magnetic field $B_0$ in the range of, for example, 0.2 Tesla to 3 Tesla or more. The main magnetic field $B_0$ is approximately homogeneous in the field of view. The main magnetic field $B_o$ extends throughout the RF cabin along magnetic field lines. Different regions within the RF cabin may be subjected to stronger or weaker magnetic fields. For example, the ends of the cyromagnet 12 may have weaker magnetic field strength, but still be within the magnetic field $B_0$.

The nuclear spins of atomic nuclei of the patient are excited via magnetic radio-frequency excitation pulses that are transmitted via a radio-frequency antenna, shown in FIG. 1 in simplified form as a body coil 18, and/or possibly a local coil arrangement. Radio-frequency excitation pulses are generated, for example, by a pulse generation unit controlled by a pulse sequence control unit. After being amplified using a radio-frequency amplifier, the radio-frequency excitation pulses are routed to the body coil 18 and/or local coils.

The gradient coils 14 radiate magnetic gradient fields in the course of a measurement in order to produce selective layer excitation and for spatial encoding of the measurement signal. The gradient coils 14 are controlled by a gradient coil control unit that, like the pulse generation unit, is connected to the pulse sequence control unit.

The signals emitted by the excited nuclear spins are received by the body coil 18 and/or at least one local coil arrangement. The body coil 18 is a single-part or includes multiple coils. The signals are at a given frequency band. For example, the MR frequency for a 3 Tesla system is about 123 MHz+/−500 KHz. Different center frequencies and/or bandwidths may be used.

In some MR tomography procedures, images having a high signal-to-noise ratio (SNR) may be recorded using local coil arrangements (e.g., loops, local coils). The local coil arrangements (e.g., antenna systems) are disposed in the immediate vicinity of the examination subject on (anterior) or under (posterior) or in the patient. The received signals are amplified by associated radio-frequency preamplifiers, transmitted in analog or digitized form, and processed further and digitized by a receiving unit. The recorded measured data is stored in digitized form as complex numeric values in a k-space matrix. An associated MR image of the examination subject may be reconstructed using a multidimensional Fourier transform from the k-space matrix populated with values. For a coil that may be operated both in transmit and in receive mode, such as the body coil 18 and/or the local coil, correct signal forwarding is controlled using an upstream-connected duplexer 18.

From the measured data, an image processing unit generates an image. The image is displayed to a user via an operator console and/or stored in a memory unit. A central computer unit controls the individual system components.

In the course of an MR measurement, the excited nuclei induce a voltage in the individual antennas of the local coil. The induced voltage is amplified by a low-noise preamplifier (e.g., LNA, preamp) and forwarded to receive electronics. High-field systems (e.g., 1.5 T or 3 T and more) are also used in the case of high-resolution images in order to improve the signal-to-noise ratio. Since more individual antennas may be connected to an MR receiving system than there are receivers present, a switching array (e.g., RCCS) is installed between the receive antennas and the receivers. The switching array routes the currently active receive channels (e.g., the receive channels currently lying in the field of view of the magnet) to the receivers present. This enables more coil elements to be connected than there are receivers present, since in the case of whole-body coverage, only the coils that are located in the field of view or in the homogeneity volume of the magnet are to be read out.

The PET detectors 16 are crystals or other photon detectors. For example, the detectors 16 are scintillation crystals coupled to avalanche photo diodes. In other embodiments, scintillation crystals are coupled with photomultiplier tubes. The scintillation crystals are bismuth germanium oxide, gadolinium oxyorthosilicate, or lutetium oxyorthosilicate crystals, but other crystals may be used.

The detectors 16 are arranged individually or in groups. The detectors generate three analog signals, two position signals and one energy signal. Each of the signals is output as a differential signal pair. The PET detectors 16 are positioned in the bore of the MR portion.

Interference in the signal chain may be introduced by this positioning. By being within the RF cabin, the PET detectors 16 are within the magnetic field generated by the cyromagnet 12. Being within the core of the cyromagnet 12, the PET detectors 16 are subjected to similar $B_o$ magnetic field strength and uniformity as the patient.

Coaxial, twisted pair, or other cables provide the signals from the PET detectors 16 to the DAU 22. Each PET signal is to be quantized and time stamped by the PET DAU 22. Since the DAU 22 is located within the RF cabin (e.g., in the same housing or shroud as the coils 14, 18 or on the filter plate), noise from the PET DAU should be reduced to a minimum. Achieving high levels of bi-directional attenuation at the MR frequency, for both differential and common signals, prevents interference with the MR imaging. With sufficient attenuation, both MR and PET scans may be performed at a same time.

Figure 2:
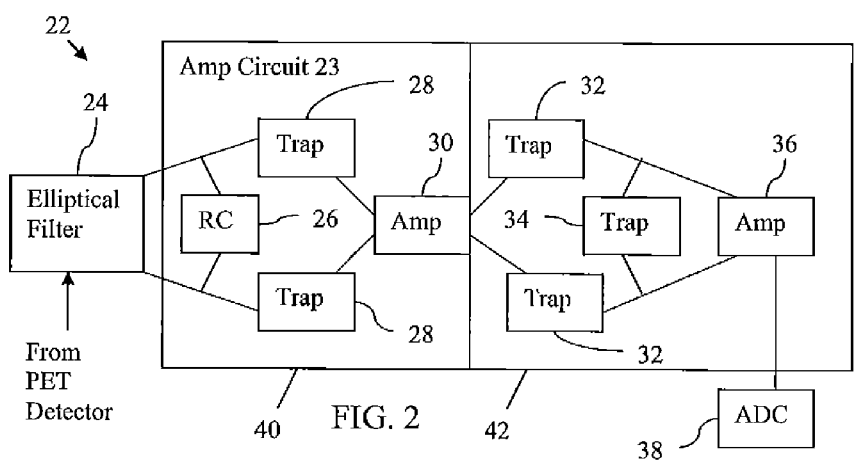
FIG. 2 is a block diagram representing a circuit, according to one embodiment, for amplification of PET signals in a hybrid PET/MR system.
Figure 3:
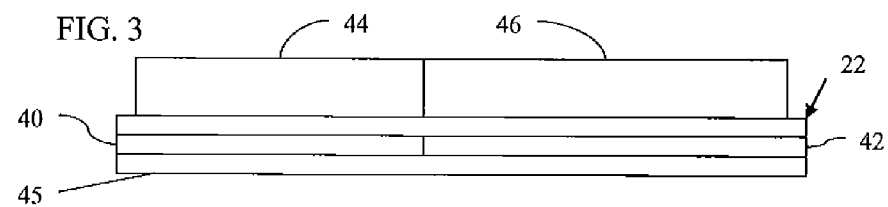
FIG. 3 is a graphical representation of a stack of components for the circuit of FIG. 2.

FIG. 2 shows one embodiment of the DAU 22. The DAU 22 includes an elliptical filter 24, an amplifier circuit 23 and an analog-to-digital converter 38. Additional, different, or fewer components may be provided. For example, a processor determines time stamps for different quantized measurements. As another example, a converter for converting electrical signals to optical signals is provided. FIG. 2 represents a filtering, amplification, and digitization path for one signal. Additional such components are provided for other signals, such as for each of the energy and position signals from each of the PET detectors 16.

As represented in FIG. 1, the DAU 22 is positioned within the magnetic field. Multiple DAUs 22 are provided, such as one for each pair of cassette of PET detectors 16. The DAUs 22 are positioned in a circular pattern partly or completely around the patient bore at one end of the cyromagnet 12 and coils 14, 18. For example, twenty eight DAUs 22 are in a radial pattern around the core on an end of an MR system. The DAUs 22 do not block access to the patient bore. By being wedge shaped, the DAUs 22 are efficiently spaced in a cylinder layout around the core opening. Other shapes may be used, such as rectangular. In other embodiments, the DAUs 22 are positioned along a side of the MR portion, such as opposite MR electronics. In yet other embodiments, the DAUs 22 are positioned in a separate standalone housing or the filter plate.

The components of each DAU 22 are arranged in one or more housings 44, 46 on one or more circuit boards 45. For example, a multi-layer circuit board is provided for the amplifier circuit 23 and the ADC 38. A separate circuit board is provided for the elliptical filter 24. Another separate circuit board may be provided for power routing, conversion to optical, or other components. The circuit board for the amplifier circuit 23 is wedge shaped or has another shape. The components of the DAU 22 are positioned on one side or group of layers of the circuit board with power routing being provided on the other side or group of layers.

The layers may be separated by one or more ground planes 40, 42. The ground planes 40, 42 are electrically separate. A RLC circuit may connect the two ground planes 40, 42 together rather than providing a common ground plane. Alternatively, the ground planes 40, 42 are not connected. One ground plane 40 is positioned on the circuit board 45 below analog components. Another ground plane 42 is positioned below digital components, such as the ADC 38. The ground planes 40, 42 extend laterally over a width of the board 45, but separate a length or longest dimension of the circuit board 45 into different regions. Other arrangements may be used. The circuit board 45 may include grounding traces or other electrical isolation separating different components and/or portions of the board 45.

Two housings 40, 42 are shown, but only one or three or more housings 40, 42 may be provided. The housings 40, 42 are metal or other conductive material, such as copper or copper plated aluminum. The housings 40, 42 are grounded, such as connected to a common ground with the MR components or a separate common ground for the DAUs 22. The housings 40, 42 mate or align with grounding isolation traces on the circuit board 45 to isolate separate parts of the DAU 22. The housings 40, 42 separately shield the electrical components of the DAU 22 for EMI. The components of the DAU 22 are within a chamber formed by the respective housing 40, 42. In one embodiment, the separate housings 40, 42 separately cover the portions of the circuit board 45 associated with the separate ground planes 40, 42.

Referring again to FIG. 2, the elliptical filter 24 is a passive filter with an elliptical filtering response. The elliptical filter 24 has an equalized ripple behavior in both the pass band and the stop band. The amount of ripple in each band is independently adjustable. Any now known or later developed elliptical filter 24 may be used. The elliptical filter 24 protects active electronics (e.g., amplifiers) from the RF burst at 123 MHz and provides attenuation at the MR frequency. In alternative embodiments, a different type of filter is provided or no filter is used prior to the amplifier circuit 23.

The elliptical filter 24 connects between the PET detectors 16 and the amplifier circuit 23. The differential signals from the PET detectors 16 are filtered prior to being passed to the amplifier circuit 23 and/or prior to amplification. The elliptical filter 24 feeds the amplifier 30 of the amplifier circuit 23. The filter traps 28 connect with the differential outputs from the elliptical filter 24. The elliptical filter 24 maintains the amplifiers in their linear operation range during RF bursts.

The amplifier circuit 22 is for amplification of the PET signals of the hybrid PET/MR system 10. The amplifier circuit 22 includes traps 28, 32, and 34, amplifiers 30, 36, and a resistor-capacitor (RC) network 26. Additional, different, or fewer components may be provided. For example, only traps 28 or 32 are provided with the trap 34. As another example, different filtering arrangements, such as additional filters, are provided. In yet another example, only one or more than two amplifiers are provided. In one embodiment, the amplifier circuit 22 is a dual balanced differential amplifier PET front end topology, with integrated parallel and series filter networks. The amplifier circuit 22 provides a well behaved transient response (little ringing) in order to minimize the impact on PET coincidence performance with MR.

The RC network 26 includes one or more resistors and one or more capacitors. Inductors may alternatively or additionally be provided. In one embodiment, a resistor and a capacitor connect in series with each other from each differential input of the amplifier 30 to ground. The RC network 26 connects across the inputs of the differential amplifier 30 to ground. The traps 28 may be connected on either side of the RC network 26 and operate in conjunction with the RC network 26. The RC network 26 is configured (e.g., components used and the values) to maintain an input impedance at the MR frequency. For example, the RC network 26 connects across input pins of the amplifier circuit 23 with a 100 ohm or other resistance to maintain the input impedance at the 123 MHz pole frequency.

The amplifier circuit 23 is a differential amplifier circuit connected with the PET detectors 16. The signal chain to the ADC 38 is full differential, but single-ended signal lines may be used.

The amplifier circuit 23 includes two or more amplifiers 30, 36. Each amplifier 30, 36 is a same type of device, but different types of devices may be used. Both amplifiers 30, 36 are differential, but may be single-ended.

In one embodiment, the first amplifier 30 for receiving signals from the elliptical filter 24 is a buffer amplifier. The amplifier 30 is powered by dual analog power supply, but may operate with a single ended power supply. The analog signals from the detectors 16 are amplified by the amplifier 30. Any gain may be provided, such as unity gain.

The amplifier 30 is positioned on the circuit board 45 in the analog region associated with the analog ground plane 40. Other positions may be used. The analog ground plane 40 shields the adjacent amplifier 30, preventing or limiting EMI.

The differential output of the amplifier 30 is input to the amplifier 36. The amplifier 36 is a flash amplifier. The buffer amplifier 30 drives the flash amplifier 36. The amplifier 36 is powered by a single-ended power supply, but may operate with a dual power supply. Any gain may be provided, such as unity gain.

The amplifier 36 is positioned on the circuit board 45 in the digital region associated with the digital ground plane 42. Other positions may be used. The digital ground plane 42 shields the adjacent amplifier 36, preventing or limiting EMI.

The ADC 38 is also positioned adjacent to (e.g., over) the digital ground plane 42. The flash amplifier 36 is positioned as close as possible to the ADC 38. Where some spacing is required, the amplifiers 36 for the energy signal are positioned closer to the respective ADCs 38 than the amplifiers 36 for the position signals are to the respective ADCs 38. Other arrangements may be used.

The differential amplifier circuit 23 is DC coupled. A DC path is provided through inductors.

The traps 28, 32, and 34 are filters for reducing or substantially eliminating signal components at the MR center frequency or frequency band. Substantially provides for −60 dB or more reduction. Less reduction may be provided. For a 3 Tesla MR cyromagnet 12, the filters reduce the signals in a band around 122 or 123 MHz, such as a 1 MHz band centered at 122 MHz being at −60 dB for the amplifier circuit 23 or each trap 28, 32, and 34, in the forward direction (i.e., response of the amplifiers driven by the detectors as seen by the ADC). In the reverse direction (i.e., from the ADC to the detectors), the attenuation may be up to or over 100 dB due the dual amplifier architecture/stages (e.g., amplifiers separated on the analog and digital ground planes) and the output impedance of the amplifiers.

The traps 28, 32, and 34 are passive RC, RL, LC, or RLC filters. Any combination of series and parallel arrangements may be used. For example, the parallel traps 28 and 32 include one or more capacitors and one or more inductors in parallel. The traps 28 may include a series resistor and/or a resistor to ground. In one embodiment, the traps 28 are 122 MHz series pole filters with a resistor to the analog ground 40 to provide a differential termination at a desired resistance. The traps 32 may not include a resistor. In one embodiment, the traps 32 are two 122 MHz series poles. As another example, the series trap 34 includes one or more capacitors and one or more inductors in series with a parallel resistor. In one embodiment, the trap 34 is a 122 MHz zero filter. Other combinations of filter components may be used, including active filter components.

The series trap 34 is configured to substantially short the signal components at the MR frequency band. Substantially shorting provides for electrical connection in a restricted manner (e.g., 60 dB difference) between the two terminals (e.g., differential inputs to the amplifier 36) at the MR frequency. At other frequencies, the trap 34 does not short or shorts less, passing the signals to the amplifier 36.

The parallel traps 28 and 32 are configured to substantially open at the MR frequency band. Substantially open provides for electrical disconnection for most (e.g., 60 dB difference) of the signal components at the MR frequency band. The MR frequency components are prevented from passing in either direction. Bi-directional attenuation is provided in the amplifier circuit 23 at the MR frequency or frequency band.

Figure 4:
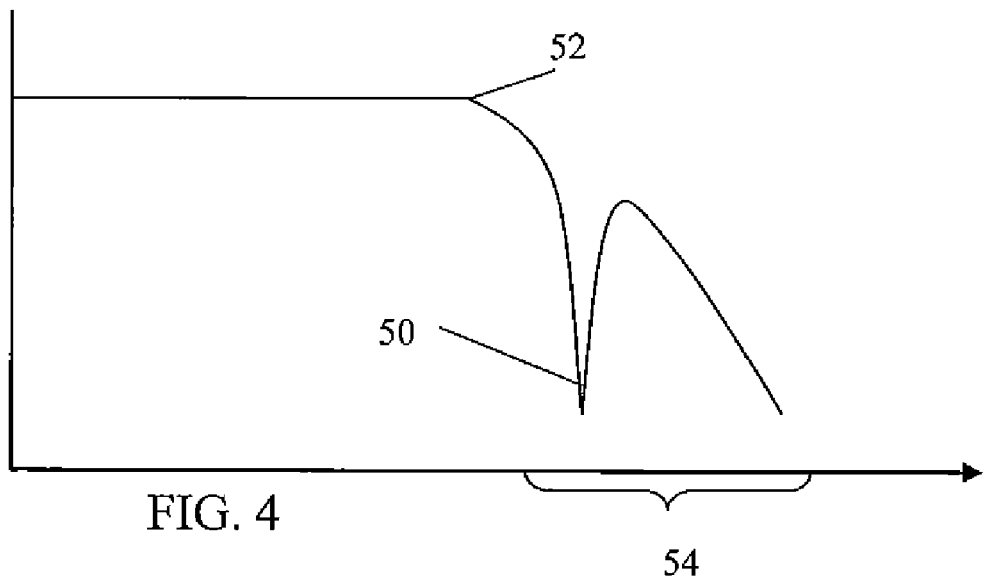
FIG. 4 is a graphical illustration of an example frequency response of an amplification circuit.

FIG. 4 represents an example frequency response of the amplifier circuit 23 in a logarithm scale along frequency. The response is a low pass response for passing PET signals below the corner frequency 52. Any corner frequency below the MR frequency may be used. In the example of FIG. 4, the corner frequency 52 is about 30 MHz. Greater or lesser pass bands may be used. The roll-off portion 54 has a gradual reduction in components at higher frequencies, such as being 3 dB down at 30 MHz and 6 dB down at 42.5 MHz. The traps or filters of the amplifier circuit 23 alter the roll-off to provide a narrow band rejection spike 50 at the MR frequency within the roll-off. For example, the spike 50 is over 80 dB down at 120.5 MHz. Wider or narrower bands may be provided for the spike 50. Greater or lesser attenuation may be provided. After the spike (i.e., at greater frequencies), the frequency response returns to the more gradual roll-off. Other frequency responses may be provided.

Referring again to FIG. 2, the traps 28 connect with the differential inputs of the amplifier 30. One trap 28 is provided along each input path. The differential signal input pins from the detector 16 drive the traps 22. The traps 28 block or filter the 123 MHz MR radio frequency voltage from being seen by the ADCs 38 both differential and single-ended and prevent any noise from the DAU 22 at 123 MHz from interfering with the MR.

The traps 32 connect with the differential outputs of the amplifier 30 and the differential inputs of the amplifier 36. For example, the traps 32 connect the output of the buffer amplifier 30 to the input of the flash amplifier 36. One trap 32 is provided for each of the differential outputs. The traps 32 block or filter the 123 MHz MR RF voltage from being seen by the ADCs 38 both differential and single ended and prevent any noise from the DAU digital section from getting back to the analog section at 123 MHz and interfering with the MR.

The trap 34 connects between the inputs of the differential amplifier 36. The trap 34 connects to the inputs between the traps 32 and the amplifier 36. For example, the trap 34 is across the differential input resistors. Other connections are possible. The trap 34 reduces the signals at the MR frequency in both directions.

The ADC 38 connects with the outputs of the amplifier 36. The ADC 38 has differential inputs. As shown in FIG. 2, the ADC 38 receives the output from the amplifier circuit 23. In one embodiment, the ADC 38 is on the same board 45 and adjacent to and in the region of the digital ground plane 42. The ADC 38 is spaced further from the amplifier 30 than the amplifier 36. In other embodiments, the ADC 38 is in a different region or on a different board. The ADC 38, like the amplifier circuit 23, is within the MR magnetic field.

In one embodiment, different types of amplifiers 30, 36 are provided for the energy and position PET signals. For example, the amplifiers 30, 36 for the energy PET signals are low noise, low distortion, low cost voltage feedback amplifier with a bandwidth of 410 MHz (unity gain), but other devices with other bandwidths may be used. The amplifiers 30, 36 for the energy signals have little temperature drift for a voltage input offset of 1.25 uV/° C. typical and a quiescent current of 22.5 mA maximum.

The bandwidth for the energy signals from the detector input to the ADC input may be set by capacitors in the feed back of both the amplifiers 30, 36. In one embodiment, the bandwidth has a 3 dB point of about 60 MHz. Other bandwidths may be provided.

For the position PET signal, the amplifiers 30, 36 are low noise, low distortion, low cost voltage feedback amplifiers with a bandwidth of 110 MHz (unity gain), but other devices with other bandwidths may be provided. The amplifiers 30, 36 for the position signals have little temperature drift for a voltage input offset of 3.0 uV/° C. typical and a quiescent current of 3.6 mA maximum.

The bandwidth for the position signals from the detector input to the ADC input may be set by capacitors in the feed back of both the amplifiers 30, 36. In one embodiment, the bandwidth has a 3 dB point of about 10 MHz. Other bandwidths may be provided.

Figure 5:
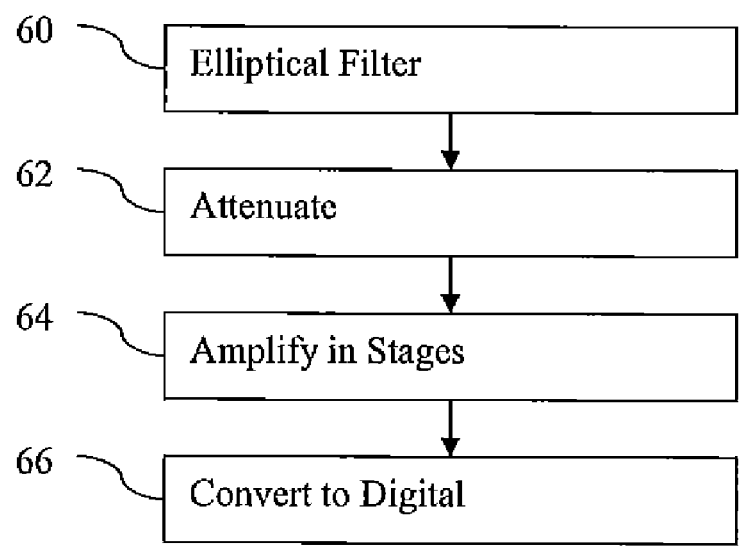
FIG. 5 is a flow chart diagram of an example embodiment of a method for amplifying positron emission tomography (PET) signals in a hybrid magnetic resonance (MR) and PET system.

FIG. 5 shows one embodiment of a method for amplifying positron emission tomography (PET) signals in a hybrid magnetic resonance (MR) and PET system. The method is implemented using the system 10 of FIG. 1, the DAU 22 of FIG. 2, the amplifier circuit 23 of FIG. 2, or other systems or circuits. The method is performed in the order shown, but other orders may be used. For example, the attenuation and amplifying of acts 62 and 64 may be intermixed or reversed. Additional, different, or fewer acts may be provided, such as digital processing, pre-amplification, and/or time stamping. For example, the elliptical filtering of act 60 is not provided.

In act 60, PET signals are filtered with an elliptical filter. The signals sensed, measured, or detected from PET detectors are filtered. The energy and position signals are filtered separately. The signals are analog, so the filtering is analog. Other filtering responses than elliptical may be used.

The elliptical filtering is performed prior to amplification, attenuation of signals at the MR frequency band, and analog-to-digital converting. In other embodiments, the elliptical filtering occurs after, at least part of, the attenuating and/or amplifying.

In act 62, the PET signals are bi-directionally attenuated at the MR frequency band. The peak attenuation is at the MR center frequency, such as the hydrogen or other molecule spin frequency. The peak attenuation may be at other frequencies within or near the MR center frequency. The bandwidth of the attenuation covers the bandwidth of RF operation of the MR system, such as 123 MHz+/−500 KHz. For the MR frequency band, the signals are attenuated by 10, 20, 30, 40, 50, 60, or more dB. Frequency components of the PET signals below, above, or above and below the MR frequency band are passed or attenuated less. For example, PET signals below 30 MHz are not attenuated or attenuated by less than 3 dB. In one embodiment, the attenuation occurs primarily in a roll-off portion of an overall response of the amplification. The roll-off portion includes a spike or relatively narrow band rejection within the roll-off, causing the roll-off to have both decreasing and increasing amounts of attenuation rather than only gradual decreasing.

The attenuation is bi-directional. Resonance feedback along the PET processing path from detection to conversion to digital may be limited by attenuating regardless of direction. Noise at the MR frequency band in the PET signals is removed to prevent radiation of EMI at the MR frequency. The bi-directional attenuation avoids interference with the detection and processing of the MR information.

The attenuation is performed by filtering. Active or passive filters remove information. For example, parallel traps prevent propagation of signals at the MR frequencies along the processing path. As another example, series traps prevent differential amplification of signals at the MR frequencies.

In act 64, the PET signals are amplified. Any gain may be provided. The amplification occurs in stages. At least two stages of amplification are used, but only one stage may be provided. Multiple stages allow for more rejection of signals at the MR frequency than would be possible by applying the full gain in one stage. The attenuating of act 62 may be performed for each stage. The PET signals are attenuated at the MR frequency. Any remaining component at the MR frequency may be amplified. Since a staged approach is used, these remaining, amplified MR frequency components may be further attenuated before more amplification. At least part of the attenuation occurs between the stages. Attenuation may be performed before, after, or before and after the amplification.

The amplification is in the analog domain. The position and energy PET signals are amplified. The amplification occurs within the radio frequency cabin around the hybrid MR and PET system. For example, the amplification is performed on a filter plate, adjacent to a magnet, within a same freestanding structure, and/or in a separate freestanding structure.

In act 66, the PET signals are converted from an analog format to the digital format. Any sampling may be used. The amplified signals are converted to digital format for time stamping and processing. The conversion occurs after attenuation and amplification.

The digital information may be time stamped, converted into optical signals, and relayed outside of the RF cabin. The digital information is processed to detect photons in opposite directions from a same radiation decay event. PET images are generated from the detected energy and position information.

While a patient is scanned using MR, the PET scanning may also occur. Simultaneous scanning is provided for MR and PET. Since the spatial relationship is known in the hybrid system, the separate scans may be combined with little to no difference is position of the patient between scans. The PET operation is provided even with amplification within the RF cabin.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A circuit for amplification in a hybrid magnetic resonance (MR) and positron emission tomography (PET) system, the circuit comprising:
a first differential amplifier for amplifying an analog signal from a photon detector;
first and second filters connected with differential inputs of the first differential amplifier, respectively, the first and second filters configured to reduce signals at a MR frequency;
a second differential amplifier driven by outputs of the first differential amplifier;
third and fourth filters connected to the outputs of the first differential amplifier and inputs of the second differential amplifier, respectively, the third and fourth filters configured to reduce the signals at the MR frequency; and
a fifth filter connected between the inputs of the second differential amplifier, the fifth filter configured to reduce the signals at the MR frequency.

2. The circuit of claim 1 further comprising:
an analog-to-digital converter (ADC) connected with outputs of the second differential amplifier, the ADC positioned adjacent to the second differential amplifier and spaced from the first differential amplifier.

3. The circuit of claim 1 further comprising:
first and second ground planes in a circuit board, the first ground plane separated from the second ground plane along a length of the circuit board, wherein the first differential amplifier is positioned adjacent to the first ground plane and the second differential amplifier is positioned adjacent to the second ground plane; and
first and second electromagnetic interference shielding housings positioned over the circuit board to separately cover portions associated with the first and second ground planes.

4. The circuit of claim 1 wherein the first and second filters comprise series pole filters, the first differential amplifier comprises a buffer amplifier, the third and fourth filters comprise series pole filters, the fifth filter comprises a zero filter, and the second differential amplifier comprises a flash amplifier.

5. The circuit of claim 1 wherein the first differential amplifier is powered by dual analog power supply and the second differential amplifier is powered by a single-ended power supply.

6. The circuit of claim 1 wherein a frequency response has a low-pass corner frequency lower than the MR frequency with a fall-off having a narrow band rejection spike at the MR frequency within the fall-off.

7. The circuit of claim 1 further comprising a passive elliptical filter connected with the first and second filters, the passive elliptical filter for filtering the analog signal before the amplifying by the first differential amplifier.

8. The circuit of claim 1 further comprising a resistor-capacitor (RC) network connected across the inputs of the first differential amplifier, the RC network configured to maintain an input impedance at the MR frequency.

9. The circuit of claim 1 wherein the first and second differential amplifiers comprise balanced differential amplifiers.

10. A hybrid magnetic resonance (MR) and positron emission tomography (PET) system comprising:
a MR magnet for generating a magnetic field;
PET detectors within the magnetic field;
a differential amplifier circuit connected with the PET detectors, the differential amplifier within the magnetic field; and
an analog-to-digital converter connected with the differential amplifier circuit, the analog-to-digital converter within the magnetic field,
wherein the differential amplifier circuit comprises a dual balanced PET front end.

11. The hybrid MR and PET system of claim 10 wherein the differential amplifier circuit comprises first and second differential amplifiers.

12. The hybrid MR and PET system of claim 10 further comprising:
a passive elliptical filter connected between the PET detectors and the differential amplifier circuit;
wherein the analog-to-digital converter connects with an output of the differential amplifier circuit.

13. The hybrid MR and PET system of claim 10 wherein the MR magnet comprises a cryogenic coil, and wherein the differential amplifier circuit is positioned adjacent to an end of the cryogenic coil.

14. The hybrid MR and PET system of claim 10 wherein the differential amplifier circuit comprise parallel and series traps at an MR frequency, the series trap configured to substantially short at the MR frequency, and the parallel trap configured to substantially open at the MR frequency.

15. The hybrid MR and PET system of claim 10 wherein the differential amplifier circuit is DC coupled and configured to provide bidirectional attenuation at a MR frequency with a pass response below an MR frequency, a roll-off of a frequency response of the differential amplifier circuit having a narrow band rejection spike at the MR frequency within the roll-off.

16. A method for amplifying positron emission tomography (PET) signals in a hybrid magnetic resonance (MR) and PET system, the method comprising:
bi-directionally attenuating the PET signals at a MR frequency;
amplifying the PET signals in at least two stages in an analog domain, the bi-directionally attenuating being performed, at least in part, between the two stages; and
converting the PET signals to digital within a radio frequency cabin.

17. The method of claim 16 wherein bi-directionally attenuating comprises filtering with parallel and series traps.

18. The method of claim 16 further comprising filtering the PET signals with an elliptical filter prior to bi-directionally attenuating, amplifying, and converting, wherein converting comprises converting the PET signals after the bi-directionally attenuating and amplifying.

19. The method of claim 16 wherein bi-directionally attenuating comprises passing frequency components below the MR frequency and trapping components at the MR frequency in a roll-off portion of the frequency response.

20. The method of claim 16 wherein amplifying comprises amplifying position and energy signals within the radio frequency cabin around the MR and PET system.

* * * * *